United States Patent
Laveault

(10) Patent No.: US 7,468,049 B2
(45) Date of Patent: Dec. 23, 2008

(54) DUAL SYRINGE ADAPTER

(75) Inventor: Richard A. Laveault, Ft. Wayne, IN (US)

(73) Assignee: Rieke Corporation, Auburn, IN (US)

( * ) Notice: Subject to any disclaimer, the term of this patent is extended or adjusted under 35 U.S.C. 154(b) by 655 days.

(21) Appl. No.: 11/152,796

(22) Filed: Jun. 14, 2005

(65) Prior Publication Data

US 2007/0005020 A1  Jan. 4, 2007

(51) Int. Cl.
*A61M 37/00* (2006.01)
*A61M 5/00* (2006.01)

(52) U.S. Cl. ......................... 604/82; 604/191
(58) Field of Classification Search ................. 604/187, 604/192–198, 207–211, 82–89, 227–228; 222/137, 145.5
See application file for complete search history.

(56) References Cited

U.S. PATENT DOCUMENTS

| | | | |
|---|---|---|---|
| 2,112,160 A | 3/1938 | Johnson | 128/234 |
| 3,746,216 A | 7/1973 | Frederick | 222/137 |
| 4,044,757 A | 8/1977 | McWhorter et al. | 128/2 A |
| 4,150,669 A | 4/1979 | Latorre | 128/79 |
| 4,359,049 A | 11/1982 | Redl et al. | 128/218 PA |
| 4,631,055 A | 12/1986 | Redl et al. | 604/82 |
| 4,735,616 A | 4/1988 | Eibl et al. | 604/191 |
| 4,978,336 A | 12/1990 | Capozzi et al. | 604/82 |
| 4,979,942 A | 12/1990 | Wolf et al. | 604/83 |
| 5,116,315 A | 5/1992 | Capozzi et al. | 604/82 |
| 5,290,259 A * | 3/1994 | Fischer | 604/218 |
| 5,368,563 A | 11/1994 | Lonneman et al. | 604/82 |
| 5,464,396 A * | 11/1995 | Barta et al. | 604/191 |
| 5,496,284 A | 3/1996 | Waldenburg | 604/191 |
| 5,582,596 A * | 12/1996 | Fukunaga et al. | 604/191 |
| 5,651,372 A | 7/1997 | Caillouette | 128/753 |
| 5,725,499 A | 3/1998 | Silverstein et al. | 604/82 |
| 5,931,813 A | 8/1999 | Liu | 604/110 |
| 6,328,229 B1 | 12/2001 | Duronio et al. | 239/399 |
| 6,471,670 B1 | 10/2002 | Enrenfels et al. | 604/88 |
| 6,620,125 B1 | 9/2003 | Redl | 604/83 |
| 6,936,033 B2 * | 8/2005 | McIntosh et al. | 604/191 |
| 2003/0040701 A1 | 2/2003 | Dalmose | 604/87 |
| 2003/0055384 A1 | 3/2003 | Enrenfels et al. | 604/191 |

* cited by examiner

*Primary Examiner*—Nicholas D Lucchesi
*Assistant Examiner*—Rebecca E Eisenberg
(74) *Attorney, Agent, or Firm*—Woodard, Emhardt, Moriarty, McNett & Henry LLP

(57) ABSTRACT

A dual syringe adapter for attachment to a pair of side-by-side syringes includes three interconnected portions. A first portion is configured so as to snap onto a plunger head portion of each syringe so as to connect the pair of syringes and maintain plunger movement in unison. A second portion of the adapter is configured so as to snap onto a syringe body of each syringe to help maintain the connection of the two syringes. The third interconnected portion is positioned between the first and second portions and when connected prevents relative movement of the plungers into the syringe bodies. Weakened sections allow the connecting portion to be severed from the first and second portions thereby allowing plunger movement into the syringe bodies. Once severed, the connecting portion is secured to syringe tips for dispensing a mixed composition.

5 Claims, 6 Drawing Sheets

DUAL SYRINGE ADAPTER

BACKGROUND OF THE INVENTION

The present invention pertains generally to the dispensing of two materials from a pair of syringes that are position side-by-side. Each syringe includes a movable plunger and in one embodiment the amount of material being dispensed from each syringe is substantially the same due to the syringe plungers moving in unison. In an alternative embodiment of the present invention, while the syringe plungers move in unison, the inside diameter of the syringe bodies are different so as to establish a different ratio or mixing proportions for the two materials being dispensed.

More specifically, the present invention pertains to the construction and use of an adapter component that assembles to the pair of syringes. While the adapter remains assembled and intact, the plunger of each syringe is unable to be pushed into the corresponding syringe body in order to push a portion of the material out of the syringe dispensing tip. By separating one portion of the adapter from the remainder, each syringe plunger is then able to be pushed inwardly into the syringe body so that a portion of the material content stored in that syringe body can be dispensed from the syringe tip.

Dual syringe systems are known in terms of uniformly metering out the proper amounts of two different materials, such as a resin material and a hardener for an epoxy composition. A dual syringe system can be used for chemical compositions where the two components need to be separated until the mixture is ready to be used. By structurally "requiring" the syringe plungers to move together, in unison, the proper mix ratio can be guaranteed. If the desired mix ratio is not 1 to 1, then the diameter size of the hollow body of one syringe is changed so that equal travel distances result in unequal amounts of material being dispensed, i.e. something other than a 1 to 1 ratio. When the syringe body diameters are the same, the movement of the syringe plungers in unison results in dispensing an equal amount of each of the two materials.

With syringe systems of the type described, the syringe bodies are preloaded with the desired materials or products for dispensing. The syringe tips are capped so as to retain the product that is loaded into the syringe bodies and in this condition the syringe plungers are extended outwardly to their initial or starting position. The syringes are then packaged and when encased or enclosed by the packaging, this prevents the inadvertent dispensing of material or contamination of some type. However, once the package is opened, it is possible to move each plunger into the corresponding syringe body and dispense a portion of the loaded material, without any further step or manipulation being required. As such, it would be possible to inadvertently push the plungers and dispense a portion of materials. Granted, while this may be unlikely with the closing caps snapped onto the syringe tips, those caps can be removed by a small child by handling and pulling on the various component parts. It would then be possible for a portion of the material to leak out due to removal of the caps. Such handling could also result in limited movement of the syringe plungers.

In order to address these concerns, the present invention provides a dual syringe adapter that assembles to the pair of syringes so as to secure the two plungers such that they can not be inadvertently moved, i.e., pushed into the syringe body. The adapter according to the present invention is secure enough to prevent plunger manipulation by small children. When the adapter is manually severed by breaking free an intermediate connecting portion, the dual syringes are fully operable for their intended movement and use. Portions of the adapter remain connected to the pair of syringes, with one portion of the adapter connected to the pair of syringe plungers and another portion of the adapter connected to the syringe bodies. The construction and arrangement of the adapter according to the present invention not only secures the two syringes in their side-by-side arrangement, but causes the syringe plungers to move together, in unison, throughout their stroke.

Another concern directed to a dual syringe system is the utilization of the two-material mix once the two materials are dispensed from the syringe tips in the desired ratios. Often there is a reaction that takes place once the materials are mixed in order to be able to use the mixed composition in the intended manner. This is one reason to keep the materials separate until the mixed composition is desired. Since the syringe tips are spaced apart from each other, the direct dispensing from the tips deposits the two materials in two separate, spaced apart volumes. These two materials must then be mixed and the mixed composition applied to the site of intended use. It would therefore be an improvement to be able to automatically combine the two materials as they are dispensed from the syringe tips and create a single resultant flow of material existing from the dual syringe system.

The present invention addresses this concern by using the portion of the adapter that is severed or broken free from the remainder of the adapter as a material combining attachment or dispensing tip. This portion of the adapter is constructed and arranged to snap onto the syringe tips such that the two materials exiting from the syringe tips flow into a central cavity that has a single exit opening. As the two materials leave the syringe tips and flow into the mixing cavity, they are able to combine with one another and then flow out the single opening as a mixed combination.

The adapter of the present invention that includes a dual use center portion constitutes a novel and unobvious structure.

SUMMARY OF THE INVENTION

A dual syringe adapter for attachment to and use with a pair of side-by-side syringes according to one embodiment of the present invention comprises a unitary structure having three interconnected portions including a plunger head portion, a syringe body portion and a separable connecting portion positioned between the plunger head portion and syringe body portion. The separable connecting portion includes a pair of tip-receiving sleeves and a flow-connected dispensing chamber wherein in its initial, unseparated condition, the separable connecting portion functions as a blocking element to fix the spacing between the plunger head portion and the syringe body portion and when separated from the unitary structure, the separable connecting portion is constructed and arranged to fit onto the dispensing tips of the side-by-side syringes such that any material dispensed from either syringe flows into the dispensing chamber.

DETAILED DESCRIPTION OF THE INVENTION

Figure 1:
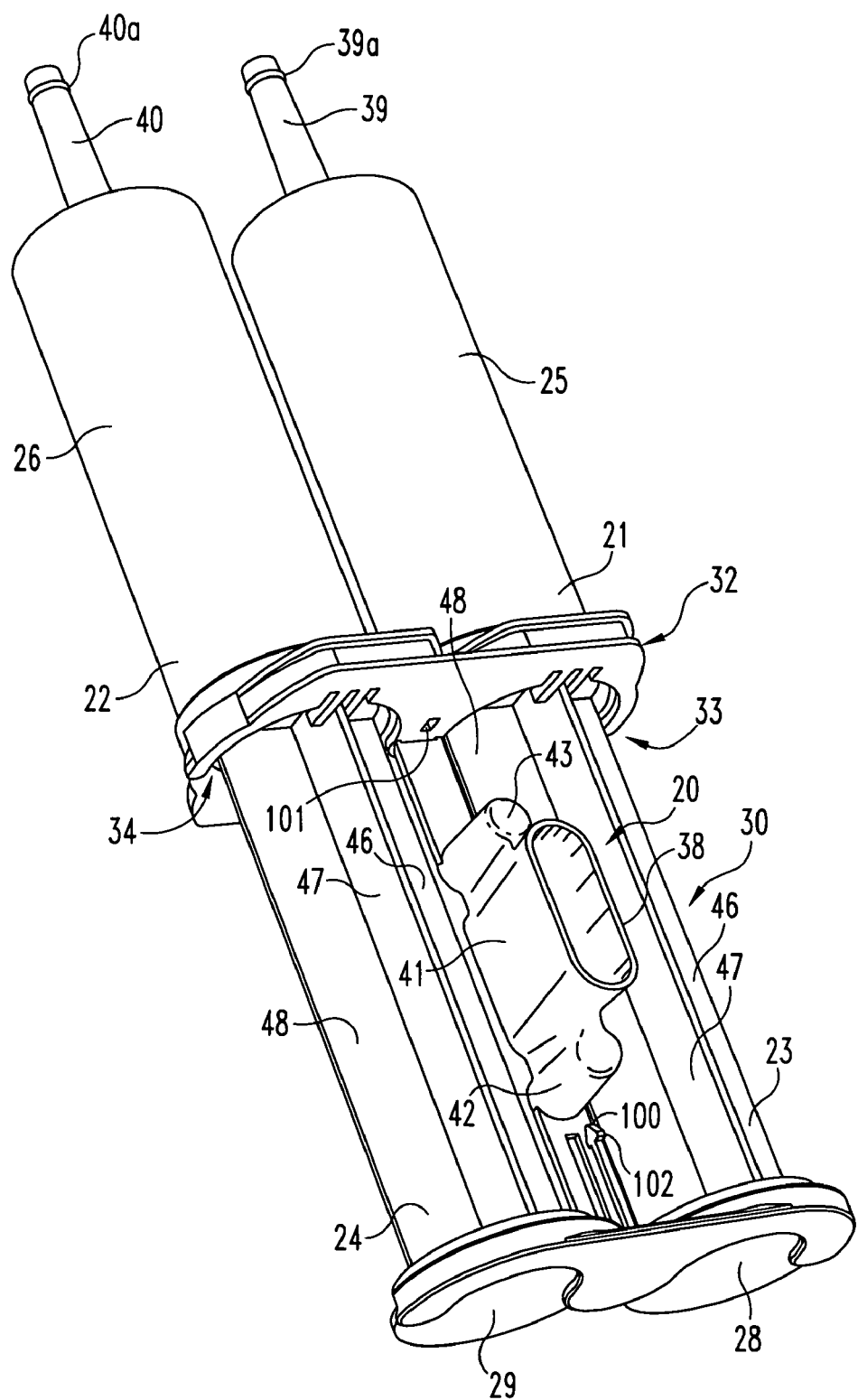
FIG. 1 is a bottom perspective view of a dual syringe adapter as assembled to a pair of syringes according to a typical embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it should be apparent to those skilled in the art that some of the features which are not relevant to the invention may not be shown for the sake of clarity.

Figure 2:
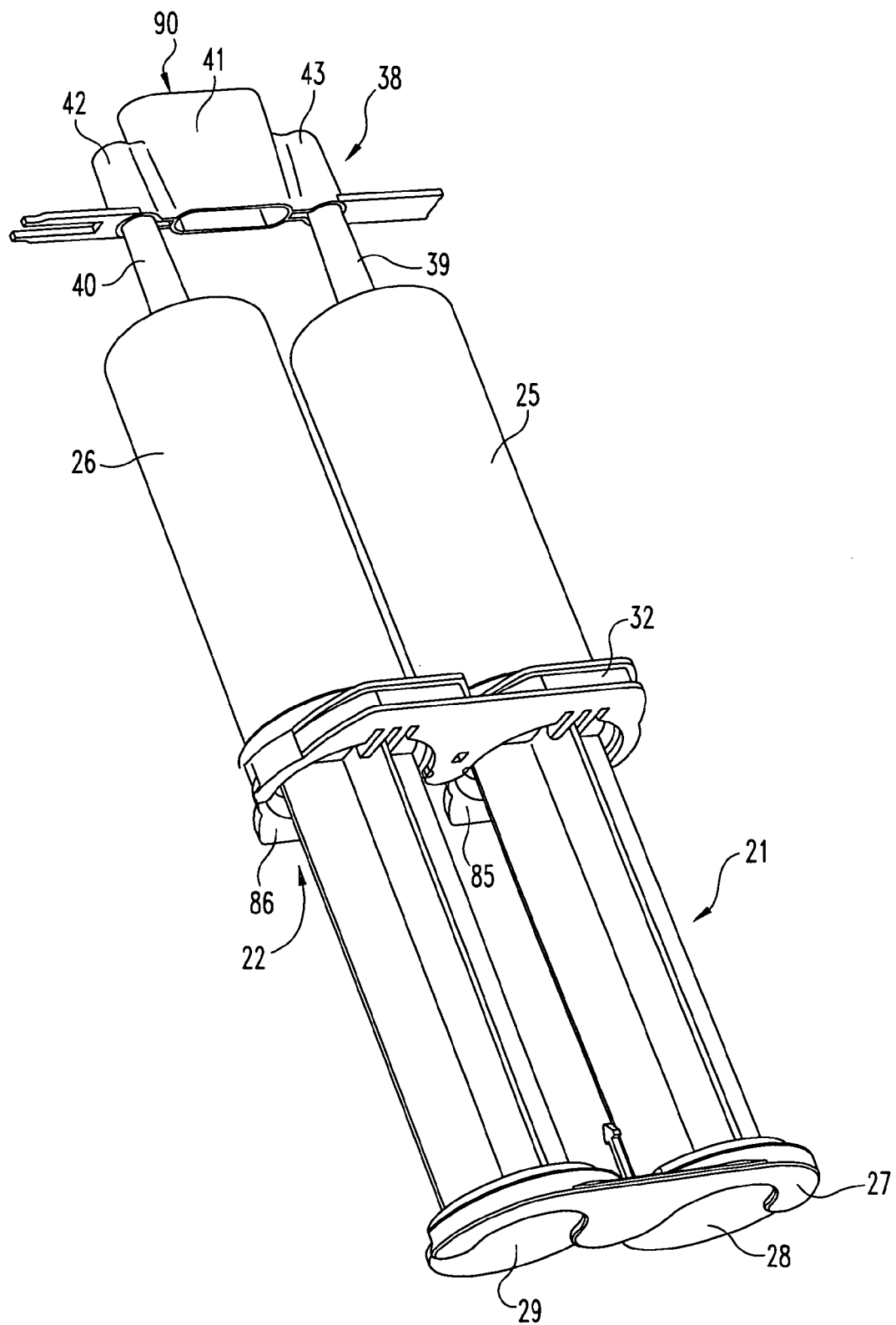
FIG. 2 is a bottom perspective view of the FIG. 1 assembly with an intermediate dispensing portion of the FIG. 1 adapter separated and assembled to the tips of the syringes according to the present invention.

Referring to FIGS. 1 and 2 there is illustrated an unitary, molded plastic dual syringe adapter 20 that is assembled to a pair of side-by-side syringes 21 and 22. In the FIG. 1 illustration the adapter 20 is depicted as initially assembled, intact, prior to use of the syringes. In this assembled configuration each syringe plunger 23 and 24 is pulled outwardly from its corresponding hollow syringe body 25 and 26, respectively, and is secured in that extended, ready for use position by the use of adapter 20. A first end 27 of adapter 20 or what could be called the plunger head portion, assembles onto the circular heads 28 and 29 of the two syringes 21 and 22, respectively, and portions of first end 27 snap onto plunger shafts 30 and 31. An opposite second end 32 of adapter 20 assembles onto each syringe body 25 and 26, adjacent their open ends 33 and 34, respectively.

The first and second ends 27 and 32 of adapter 20 are spaced apart by intermediate dispensing portion 38 that begins (see FIG. 1) integrally joined to the first and second ends 27 and 32 as part of the unitary, molded plastic construction of adapter 20. The locations of initial connection between dispensing portion 38 and the first and second ends 27 and 32 are weakened to enable the dispensing portion 38 to be manually separated (snapped off) and then utilized as illustrated in FIG. 2. By breaking or severing dispensing portion 38 free from the first and second ends 27 and 32, these two ends remain assembled to syringes 21 and 22 as illustrated in FIGS. 1 and 2, and dispensing portion 38 is able to be used for product dispensing as illustrated in FIG. 2 and as will be described in greater detail hereinafter.

As is illustrated in FIG. 2, the dispensing portion 38 is constructed and arranged to press onto the two syringe dispensing tips 39 and 40 with the hollow product cavity or chamber 41 positioned between the two dispensing tips 39 and 40. As should be understood, the molding of each syringe 21 and 22 provides as part of the corresponding dispensing tips 39 and 40, respectively, a raised annular rib or bead 39a and 40a for the purposes of assisting in the snap fit receipt of other components. In the initial assembly and filling of syringes 21 and 22 with the desired product, the dispensing tips need to be closed or sealed in some fashion so that the loaded materials do not inadvertently leak out the ends of the dispensing tips. As will be disclosed in greater detail herein, small caps are snapped onto the ends of the dispensing tips as a means to seal or close off the openings. These caps include a cooperating molded plastic construction on their interior that works with the raised annular beads 39a and 40a so as to snap onto and snap off of the corresponding dispensing tips. As will be described herein, the sleeve portions of intermediate dispensing portion 38 include raised bumps on their interior that cooperate with the raised annual beads 39a and 40a so that the dispensing portion 38 actually snaps onto the two syringe tips 39 and 40 as part of the FIG. 2 illustrated assembly. As an alternative, the hollow dispensing sleeves 42 and 43 of intermediate dispensing portion 38 can be constructed with a size and shape to provide a press fit onto dispensing tips 39 and 40, but the snap-on construction is preferred.

Syringes 21 and 22 are identical to each other and any portion of the following description that may refer only to syringe 21 should be considered as fully applicable to the structure and functioning of syringe 22 and the reverse is true as well. Any more detailed description with regard to syringe 22 would be fully applicable to the structure and functioning of syringe 21. Due to this identical construction, it is sufficient to describe only one syringe in terms of what would be required for a complete and enabling disclose. Further, a similar type of syringe is disclosed in U.S. Pat. No. 5,009,645 that issued Apr. 23, 1991 to Silver et al. The '645 patent is expressly incorporated by reference in its entirety.

Of importance to the present invention in terms of the construction and arrangement each syringe is the rail section or plunger shaft, item 18 in the '645 patent, and items 30 and 31 in FIGS. 1 and 2 of the present invention disclosure.

The plunger 30 of syringe 21 is constructed and arranged with a cruciform shape in transverse cross section, including four rails with three of the four identified as rails 46, 47, and 48. When first end 27 is assembled onto circular head 28, and the same is true for circular head 29, clip members 50 and 51 snap onto rails 46 and 48, respectively. Since the same assembly occurs simultaneously with respect to syringe 22, the first end 27 is securely attached to the pair of syringes 21 and 22, and specifically to the pair of syringe plungers 23 and 24. The circular heads 28 and 29 of the two syringes are received by first end 27 with a sliding fit into a part-circular groove and the assembly is completed by the snap-on attachment of clip members 50 and 51 to the two rails 46 and 48. Each clip member 50 and 51 is a part-circular form and the free ends 50a and 50b and 51a and 51b are constructed and arranged with an offset wedge-shaped, barb tip 50c and 51c, respectively.

First end 27 remains assembled to syringes 21 and 22 even after dispensing portion 38 is snapped off and removed. First end 27 helps to maintain the desired side-by-side spacing for syringes 21 and 22 and the physical connection of syringes 21 and 22 to each other. Additionally, first end 27 causes the inward movement of the two syringe plungers 23 and 24, into hollow syringe bodies 25 and 26, respectively, to be in unison. In terms of manual manipulation and dexterity, first end 27 also helps with the dispensing of product from the two syringes since the user can push on either syringe plunger or on first end 27 or on some combination of these three components and they will all move in unison so as to result in equal plunger travel into the syringe bodies in order the dispense product.

Second end 32 includes a pair of side-by-side part-circular portions (sleeves) 52 and 53 that are constructed and arranged to assemble onto the syringe bodies 25 and 26, respectively. A cooperating shelf portion 54 includes two sets of spaced-apart clips 55 and 56. Each pair of clips 55 and 56 defines a clearance space 57 therebetween that receives rail 47 of the corresponding syringe plunger. Each clip 55 and 56 is constructed and arranged with a barb-type tip 58 and 59, respectively, that snaps onto the inner edge of the corresponding syringe body 25 and 26. This snap-on securement ensures that the second end 32 remains attached to both syringe bodies even after dispensing portion 38 is snapped off and removed from dual syringe adapter 20.

Second end 32 helps to maintain the desired side-by-side spacing for syringes 21 and 22 and helps with the overall handling and manipulation of the two syringes 21 and 22 as the two product components or material constituents are being dispensed out of syringe tips 39 and 40.

Figure 3:
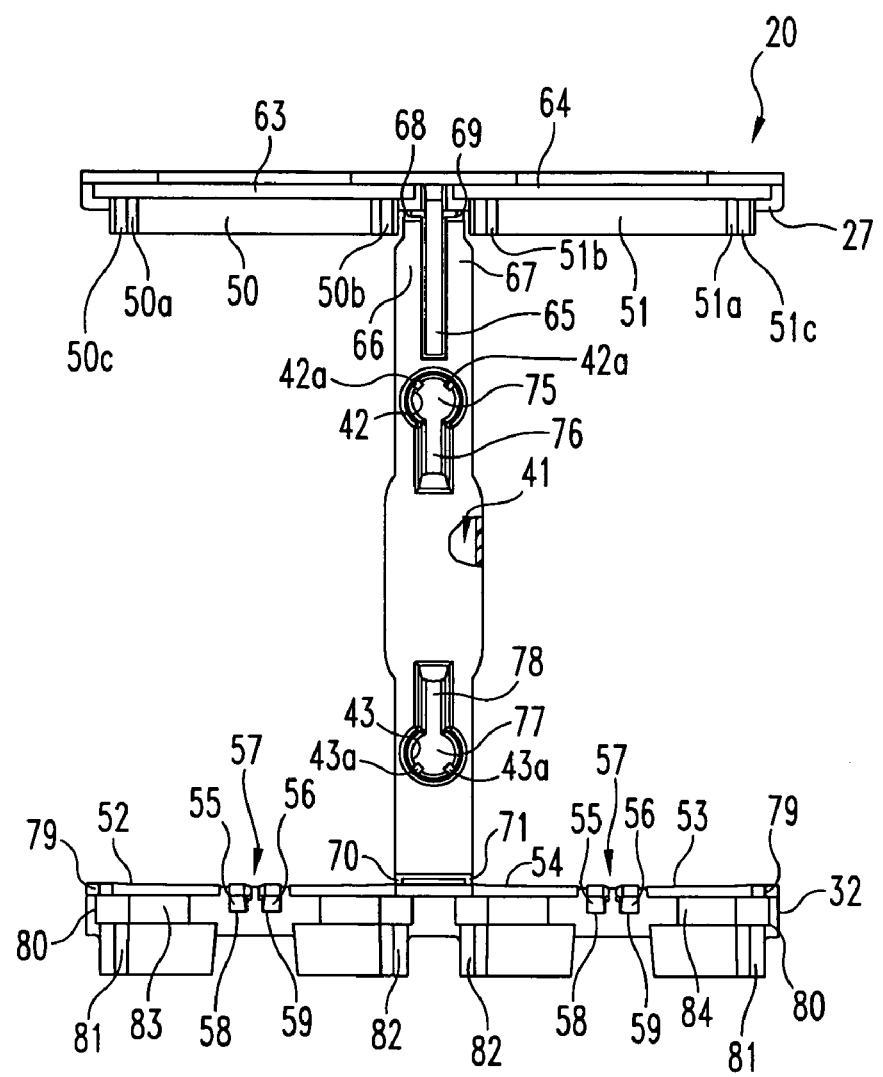
FIG. 3 is a top plan view of the FIG. 1 dual syringe adapter.
Figure 4:
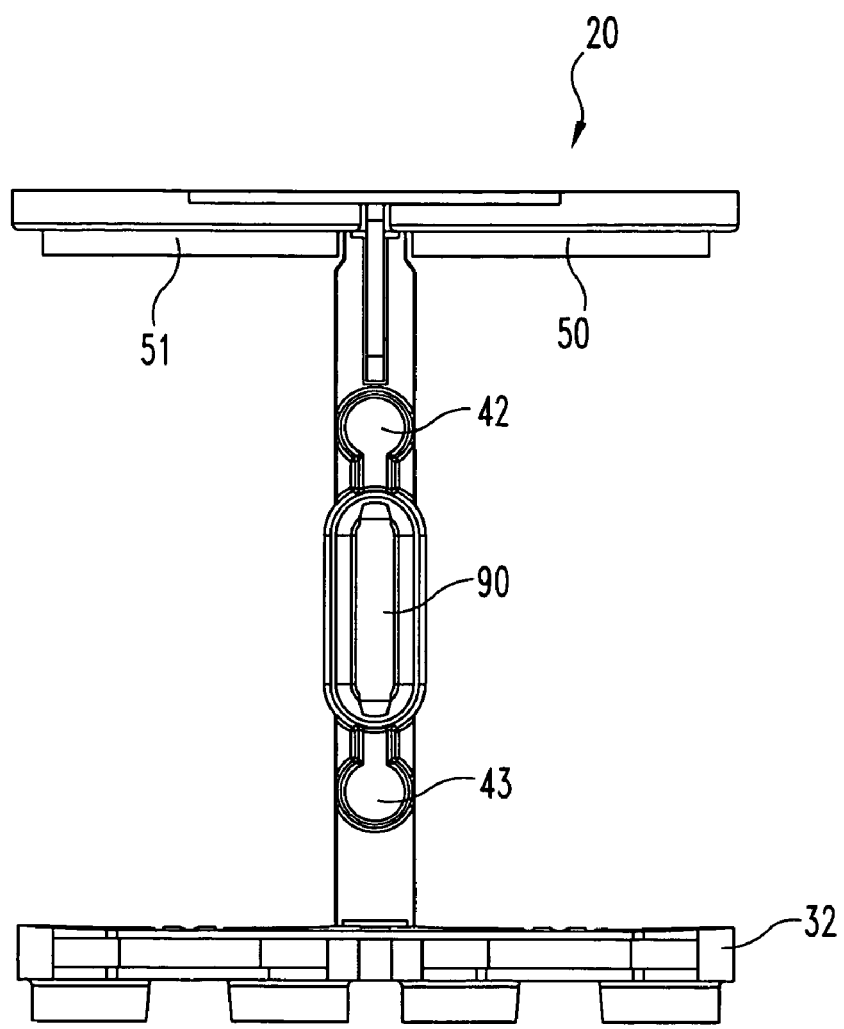
FIG. 4 is a bottom plan view of the FIG. 1 dual syringe adapter.
Figure 5:
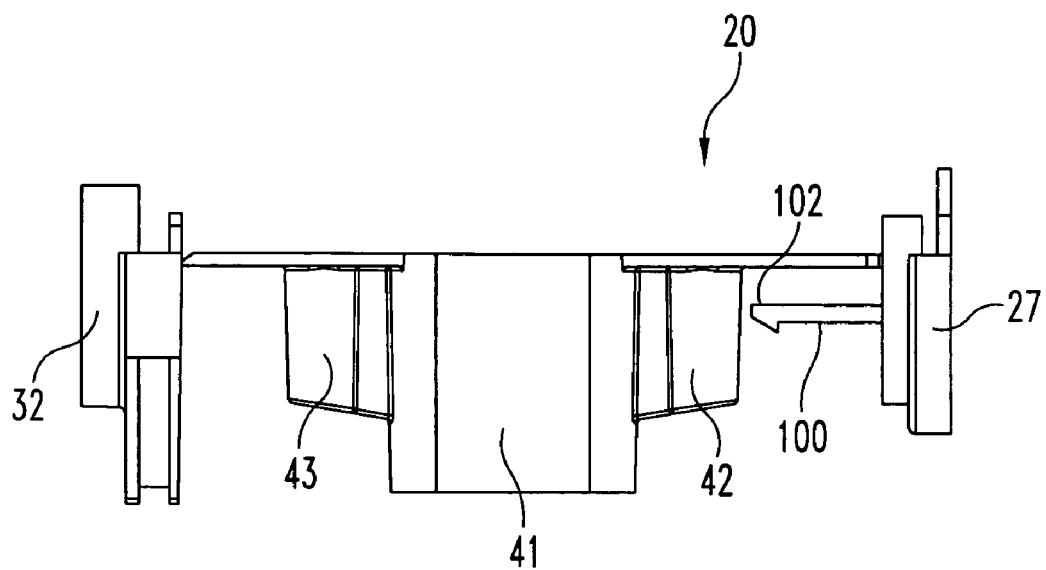
FIG. 5 is a front elevational view of the FIG. 1 dual syringe adapter.

Considering the foregoing description in terms of the general features, structure and functioning of syringes 21 and 22, and considering the cooperative nature of adapter 20, additional structural details of adapter 20 are illustrated in FIGS. 3 through 7. Referring first to FIG. 3, a top plan view of adapter 20 is provided. Repeating those structural features already described, adapter 20 includes first end 27, second end 32, intermediate dispensing portion 38, hollow product cavity 41, hollow dispensing sleeves 42 and 43, clip members 50 and 51, part-circular portions 52 and 53, shelf portion 54, clips 55 and 56, clearance space 57 and tips 58 and 59. Additionally, adapter 20 includes part-circular grooves 63 and 64 for receipt of circular heads 28 and 29, respectively. Open slot 65 is defined by connecting arms 66 and 67 and each arm is joined to first end 27 by a reduced material thickness, weakened section 68 and 69, respectively. When dispensing portion 38 is broken free or severed from first end 27, it is weakened sections 68 and 69 that are the portion broken or severed.

At the opposite end of dispensing portion 38, a pair of weakened (reduced material thickness) sections 70 and 71 are provided as the locations of connection to second end 32. Each section 70 and 71 is initially molded as part of unitary adapter 20, connecting dispensing portion 38 to shelf portion 54. When dispensing portion 38 is broken free from second end 32, it is weakened sections 70 and 71 that are severed.

The upper opening 75 of sleeve 42 includes and extended channel 76 that opens into one side of hollow product cavity 41. Similarly, upper opening 77 of sleeve 43 includes an extended channel 78 that opens into an opposite side of hollow product cavity 41. Sleeve 42, as well as sleeve 43, includes a pair of raised bumps 42a and 43a, respectively, that cooperate with the raised annual beads 39a and 40a, respectively, to facilitate the snap fit assembly of dispensing portion 38 onto syringe tips 39 and 40.

Second end 32 is constructed and arranged with a pair of part-circular portions 52 and 53 and each portion includes and upper lip 79, an offset portion 80 and clip arms 81 and 82. Upper lip 79 is a coplanar part of shelf portion 54. This structural combination defines part-circular grooves 83 and 84. As will be seen from U.S. Pat. No. 5,009,645 each syringe body 25 and 26 includes an annual flange (item 72 in the '645 patent). In FIG. 2, these annular flanges are identified as items 85 and 86 and are received within part-circular grooves 83 and 84, respectively. The interior of each groove 83 and 84 is shaped so as to be compatible with the shape, as well as the thickness, of the annular flange of the corresponding syringe.

Figure 6:
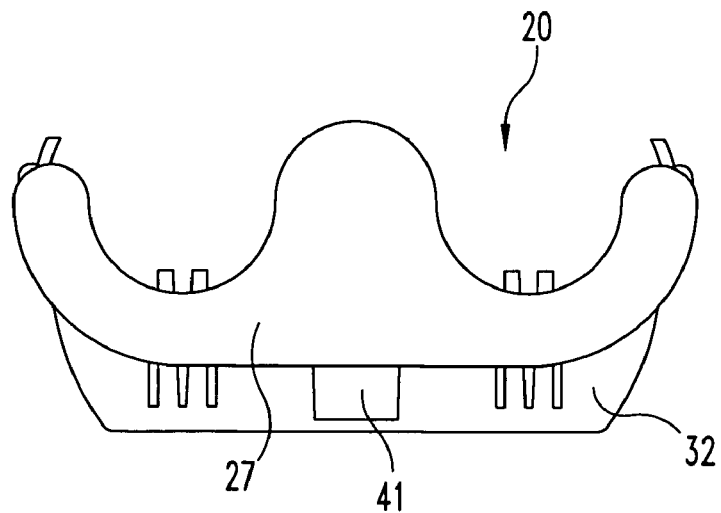
FIG. 6 is a right side elevational view of the FIG. 1 dual syringe adapter.
Figure 7:
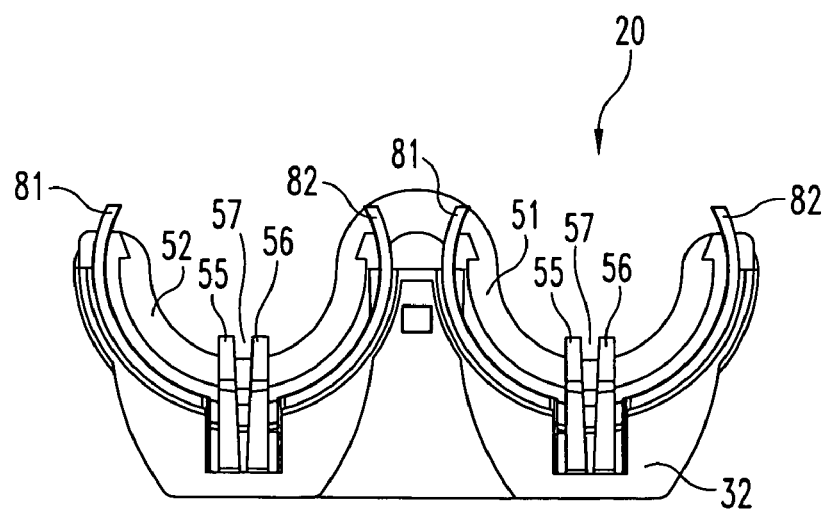
FIG. 7 is a left side elevational view of the FIG. 1 dual syringe adapter.

Referring to FIGS. 4 through 7, additional views of the dual syringe adapter 20 are provided. The additional view add structural details and clarity to those aspects and features of adapter 20 that have been described in the context of FIGS. 1 through 3. For example, it is a little easier to appreciate the part-circular form of grooves 63 and 64 based upon the FIG. 6 illustration. It is also a little easier to appreciate the part-circular form of grooves 83 and 84 from the FIG. 7 illustration. FIG. 7 also provides added clarity to the configuration of clips 55 and 56, clearance space 57, barb-tips 58 and 59 and clip members 50 and 51.

Referring again to FIGS. 1 and 2, it is intended that once the pair of syringes 21 and 22 are filled with the selected product with the desired material composition and in the desired amount, the adapter 20 is snapped onto the syringes 21 and 22 as previously described (see FIG. 1). As long as the dispensing portion 38 remains connected to and between first end 27 and second end 32, the syringe plungers 23 and 24 are not able to exhibit any noticeable movement into their corresponding syringe bodies 25 and 26, respectively, so as to dispense product out of dispensing tips 39 and 40.

By preventing any noticeable plunger movement while dispensing portion 38 of adapter 20 is connected to the first end 27 and second end 32, adapter 20 is able to provide a child-resist feature. It is not feasible for an infant or small child to be able to manipulate dispensing portion 38 so as to break it free from its connection to first and second ends 27 and 32. Whether in terms of understanding the design, having the required strength or the necessary dexterity, it is unlikely that an infant or small child would be able to defeat dispensing portion 38 or remove adapter 20 from the pair of syringes.

By manually bending the dispensing portion 38 of adapter 20 at a first location adjacent first end 27 and then at a second location adjacent second end 32, the connection locations can be broken or severed. More specifically, weakened sections 68 and 69 break so as to separate one end of dispensing portion 38 from first end 27. Likewise, weakened sections 70 and 71 break so as to separate the opposite end of dispensing portion 38 from second end 32. Once the dispensing portion 38 is broken free it is removed allowing the syringe plungers to move inwardly into their corresponding syringe bodies in order to dispense product.

The additional use of dispensing portion 38 according to the present invention is, as its name implies, for dispensing product. As briefly described above, sleeves 42 and 43 have a size, shape and spacing for snapping onto the pair of dispensing tips 39 and 40 of the dual (side-by-side) syringes 21 and 22. The hollow product cavity 41 is positioned between and is in flow communication with the two sleeves 42 and 43. As the syringe plungers are pushed into syringe bodies, in unison due to the connections provided by first end 27 and second end 32, product is dispensed from tips 39 and 40. These two products or material components, such as part A and part B of an epoxy system, flow from tips 39 and 40 into sleeves 42 and 43 and from there into cavity 41. The dispensing opening 90 at the free or exposed end of cavity 41, as defined by sidewall 91, provides the exit opening and path for the two product components that are introduced into cavity 41 to flow to the intended site of use.

It is envisioned that the two product components will be subjected to some mixing within cavity 41 and the combined composition of these two materials in the desired mix ratio is then delivered out of opening 90. Since opening 90 is able to be targeted to a specific site, the use of dispensing portion 38 provides not only a convenient way to combine and mix the two product components, but dispensing portion also provides a beneficial way to actually target the delivery of the mixed components to the intended location.

The first end 27 of adapter 20 includes an interlocking post 100 and the second end of adapter 20 includes a cooperating receiving opening 101. As product is dispensed from the pair of syringes, the first end 27 moves in the direction of second end 32. As the syringe plungers approach the base of each syringe body, denoting that location where substantially all product is dispensed, post 100 snaps into opening 101. Due to the offset or barbed tip 102 of post 100, once the post snaps into the opening, it is secured in that position. This secured or locked condition prevents the syringe plungers from being pulled back or otherwise opened by an infant or small child. This helps to prevent access to any remaining material residue. The locked condition also discourages any attempted reuse of the pair of syringes. As such, the entire assembly of the dual syringe adapter 20 and the pair of syringes 21 and 22 are considered to be disposable once the preloaded material or product is dispensed. This suggests that the end user should not attempt to introduce some other material composition that might not be compatible with the materials already dispensed. By not attempting to reuse the pair of syringes, there is no risk that incompatible materials may get mixed together.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A dual syringe adapter for attachment to and use with a pair of side-by-side syringes, said dual syringe adapter comprising:
   a unitary structure having three initially interconnected portions including a plunger head portion, a syringe body portion and a separable connecting portion positioned between the plunger head portion and the syringe body portion, said separable connecting portion including a pair of tip-receiving sleeves and a flow-dispensing cavity, wherein in its initial unseparated condition, the separable connecting portion functions as a blocking element and prevents any significant reduction in the spacing between said plunger head portion and said syringe body portion and when separated from said unitary structure, said separable connecting portion is constructed and arranged to fit onto the dispensing tips of the side-by-side syringes such that any material dispensed from either syringe flows into said dispensing cavity.

2. In combination:
   a first syringe including a hollow syringe body formed with a dispensing tip at one end and an opening at the opposite end, and a plunger inserted into said syringe body, said plunger including a plunger head; and
   a second syringe having a hollow syringe body formed with a dispensing tip at one end and an opening at the opposite end, and a plunger inserted into said syringe body, said plunger including a plunger head; and
   a dual syringe adapter for attachment to and use with said first and second syringes, said dual syringe adapter comprising:
   a unitary structure having three initially interconnected portions including a plunger head portion, a syringe body portion and a separable connecting portion positioned between the plunger head portion and the syringe body portion, said separable connecting portion including a pair of tip-receiving sleeves and a flow-dispensing cavity, wherein in its initial unseparated condition, the separable connecting portion functions as a blocking element and prevents any significant reduction in the spacing between said plunger head portion and said syringe body portion and when separated from said unitary structure, said separable connecting portion is constructed and arranged to fit onto the dispensing tips of the side-by-side syringes such that any material dispensed from either syringe flows into said dispensing cavity.

3. A method of controlling the dispensing of material contents from a pair of side-by-side syringes, said method comprising the following steps:
   providing a syringe that includes a first material for dispensing, the first syringe including a hollow body, a plunger moveable in said hollow body and a dispensing tip; and
   providing a second syringe that includes a second material for dispensing, said second syringe including a hollow body, a plunger moveable in said hollow body and a dispensing tip;
   providing a dual syringe adapter constructed and arranged as a unitary structure having three initially connected portions including a first portion, a second portion and an intermediate connecting portion;
   attaching said first portion to the plunger of said first syringe and to the plunger of said second syringe;
   attaching said second portion to the hollow body of said first syringe and to the hollow body of said second syringe, wherein said connecting portion prevents any significant inward relative motion of said syringe plungers into said corresponding syringe bodies; and
   manually severing said connecting portion from said first portion and manually severing said connecting portion from said second portion so as to enable inward movement of each plunger into its corresponding syringe body.

4. The method of claim 3 which further includes the step of assembling said severed connecting portion onto said pair of syringe tips, said connecting portion including a material cavity constructed and arranged to receive material from each syringe.

5. The method of claim 4 which further includes the step of pushing each of said plungers into its corresponding hollow body so as to dispense a portion of the material content in each syringe into said material cavity such that the two material contents exit from said material cavity as a two-material composition.

* * * * *